United States Patent [19]
Boesten et al.

[11] Patent Number: 5,916,762
[45] Date of Patent: Jun. 29, 1999

[54] PROCESS FOR THE RECOVERY OF AMPICILLIN

[75] Inventors: Wilhelmus H. J. Boesten, Sittard; Harold M. Moody; Eric C. Roos, both of Maastricht, all of Netherlands

[73] Assignee: Chemferm V.O.F., Breda, Netherlands

[21] Appl. No.: 08/940,984

[22] Filed: Sep. 30, 1997

Related U.S. Application Data

[63] Continuation of application No. PCT/NL96/00128, Mar. 25, 1996.

[30] Foreign Application Priority Data

Mar. 31, 1995 [BE] Belgium .................................. 9500291

[51] Int. Cl.$^6$ ........................... C12P 37/04; C12P 37/00; C07D 499/18; C07D 499/00
[52] U.S. Cl. ............................... 435/43; 540/317; 435/45
[58] Field of Search ......................... 435/43, 45; 540/317

[56] References Cited

U.S. PATENT DOCUMENTS

| | | | |
|---|---|---|---|
| 3,980,637 | 9/1976 | Grossman et al. ....................... | 540/317 |
| 4,351,766 | 9/1982 | Walker et al. ........................... | 540/317 |
| 4,354,971 | 10/1982 | Edmundowicz et al. ............... | 540/323 |
| 5,525,483 | 6/1996 | Kaasgaard et al. ...................... | 435/45 |

FOREIGN PATENT DOCUMENTS

| | | |
|---|---|---|
| 26 11 286 | 9/1976 | Germany . |
| 994402 | 6/1965 | United Kingdom . |
| WO 95/03420 | 2/1995 | WIPO . |

OTHER PUBLICATIONS

APS Japan Abstract 59–219291 Ishimaru et al, "Production of Antibiotic", Dec. 10, 1984.

Derwent ABS 95–075246/10 WO9503420 Boesten et al, "Recovery of D–Pheny–Glycine Amide from Antibiotic Coupling . . . ", Feb. 2, 1995.

*Primary Examiner*—Herbert J. Lilling
*Attorney, Agent, or Firm*—Pillsbury Madison & Sutro LLP

[57] ABSTRACT

Process for the recovery of ampicillin from a mixture containing ampicillin and 6-aminopenicillic acid (6-APA), in which a mixture of ampicillin and 6-APA, with a pH higher than 7, which apart from any solid ampicillin being present is homogeneous at a pH between 7 and 8.5, is subjected to a pH lowering till a pH lower than 8.2 is reached, and the solid substance present is recovered. The process is in particular suitable to be applied to the reaction mixture which is obtained after the enzymatic acylation reaction of 6-APA with a phenylglycidine derivative as acylation agent. Pure ampicillin can thus be recovered in a simple way.

12 Claims, No Drawings

PROCESS FOR THE RECOVERY OF AMPICILLIN

This is a Continuation of International Appln. No. PCT/NL96/00128 filed Mar. 25, 1996.

FIELD OF THE INVENTION

The invention relates to a process for the recovery of ampicillin from a mixture containing ampicillin and 6-aminopenicillic acid (6-APA).

BACKGROUND INFORMATION

In the preparation of ampicillin, with 6-APA being acylated with a D-phenylglycine derivative, the recovery of the ampicillin and working up of the reaction mixture are difficult in general.

A process for isolating the ampicillin pure from a mixture containing ampicillin and minor quantities of 6-APA is described in JP-A-47030687. According to the process described in this Japanese publication, an acid aqueous mixture containing 6-APA and ampicillin is subjected to an extraction with butanol or isoamylalcohol, after which the pH is raised to a value between 6 and 7 and the product is recovered by complete boiling down and freeze-drying. The drawback of this method is that organic solvents that are alien to the process have to be added. In addition, complete boiling down and freeze-drying is not industrially practicable. Moreover, the process involves formation of salts that are included in the freeze-dried product.

GB-A-994402 discloses a process wherein ampicillin is recovered from a mixture of ampicillin and aminopenicillanic acid by conversion of the ampicillin to the trialkylamine salt and recover the ampicillin as its trialkylamine salt.

SUMMARY AND OBJECTS OF THE INVENTION

The object of the invention is to provide a simple, industrially practicable process allowing ampicillin to be recovered in pure form without making use of said organic solvents that are alien to the process.

This is achieved according to the invention in that a mixture containing ampicillin and 6-APA and having a pH higher than 7, which, apart from any solid ampicillin that is present, is homogeneous at a pH between 7 and 8.5, is subjected to a pH lowering to a pH lower than 8.2, and that the solid substance present is recovered.

We discovered that by lowering the pH of the mixture to a value lower than 8.2, for instance between 5 and 8, in particular between 5.5 and 7.8, depending on the composition of the reaction mixture, it is possible to cause ampicillin to be crystallized out with a purity of more than 90 mass %, in particular more than 98 mass %, even if a large amount of 6-APA is present in the mixture, after which it can be recovered. Besides ampicillin the reaction mixture often contains other valuable components, such as for instance the 6-APA. In order to get a commercially attractive process it is consequently important also to minimize the 6-APA and ampicillin losses. It has also been found that if subsequently the pH is lowered further to a value of less than 7, in particular between 1.5 and 6, 6-APA and the remaining ampicillin crystallizes out virtually completely, after which this mixture of 6-APA and ampicillin can be recovered, for instance by filtration. The resulting mixture of 6-APA and ampicillin can optionally be re-used, so that a process is obtained which yields pure ampicillin without significant losses of 6-APA and ampicillin.

DETAILED DESCRIPTION OF THE INVENTION

The process according to the invention is in particular suitable to be applied in the working up of the reaction mixture which is obtained after the enzymatic acylation reaction in which 6-APA is acylated with D-phenylglycine amide (PGA) or esters of D-phenylglycine. Thus, the process according to the invention can for instance be applied to a starting mixture that is obtained by successively filtering, with isolation of (immobilized) enzyme, the reaction mixture of an enzymatic acylation reaction carried out at a relatively high pH, for instance a pH between 7.5 and 10, in particular between 8 and 10, lowering the pH to a value between 7 and 9. Depending on the amount of D-phenylglycine (PG) formed during the acylation reaction, if desired, it is possible to remove first at a higher pH-value between 7 and 9—which is selected dependent on the mixture such that already PG has been crystallized out and ampicillin has not yet—the eventually formed solid substance, which mostly will consist mainly of PG.

In another embodiment the starting mixture used is the mixture obtained after an enzymatic acylation reaction that ends at a relatively low pH, for instance a pH between 7 and 8.8, preferably between 7.5 and 8.8, and after isolation of the solid substance which mainly contains the immobilized enzyme and D-phenylglycine.

In the starting mixture containing 6-APA and ampicillin, a significant quantity of 6-APA may be present. The quantity of 6-APA is mostly less than 75 mol % relative to the total amount of 6-APA plus ampicillin, preferably 2–60%, in particular 5–50%.

The pH may be lowered in several ways in the framework of the invention, for instance chemically by adding an acid, for instance a mineral acid, in particular sulphuric acid, hydrochloric acid or nitric acid. Another possibility is for instance, if PGA has been used as acylation agent in the acylation reaction or if an ester of PG has been used and the pH has been kept constant by means of titration with ammonia during the acylation reaction, to lower the pH through physical removal of ammonia. Suitable physical removal methods are for instance stripping with steam or an inert gas; (steam) distillation at reduced pressure, in particular thin-film evaporation; evaporation in a spray tower; gas membrane separation or electrodialysis.

The optimum pH at which ampicillin is recovered depends on the composition of the mixture and is chosen such that optimum separation of 6-APA and ampicillin is achieved. In practice the optimum pH is a compromise between on the one hand high purity of the ampicillin recovered, which is achieved if the pH at which the ampicillin is recovered is relatively high, so that the ampicillin is still partly in solution and the 6-APA still completely in solution, and on the other hand a high yield, which is achieved if the pH at which the ampicillin is recovered is relatively low so that the ampicillin has been precipitated virtually completely, while at the same time part of the 6-APA has also been precipitated. For the person skilled in the art it is easy to determine the optimum pH in a given situation.

The temperature at which the working up is performed is mostly lower than 35° C., preferably between 0 and 30° C., in particular between 10 and 30° C.

The process according to the invention for recovery of pure ampicillin in combination with recirculation of the mixture of 6-APA and ampicillin obtained after further pH lowering, applied to the mixture obtained after enzymatic acylation of 6-APA with PGA enables an overall high selectivity towards 6-APA to be achieved, in particular higher than 80%. The remaining filtrate, which mainly contains minor residual amounts of PGA, may optionally be worked up further, for instance by bringing it to a pH higher than 8, in particular between 8.5 and 10. If desired, it is possible to apply further concentration and cooling to a temperature lower than 10° C., for instance between 0 and 8° C. In this way a process is obtained with which both 6-APA and PGA can be applied with a high efficiency. In the enzymatic acylation reaction, PGA or esters of PGA for instance may be used as acylation agent.

In principle any enzyme can be used that is suitable as catalyst in the coupling reaction. Such enzymes are for instance the enzymes that are known under the general designations 'penicillin amidase' and 'penicillin acylase'. Examples of suitable enzymes are enzymes derived from Acetobacter, Aeromonas, Alcaligenes, Alcaligenes, Aphanocladium, Bacillus sp., Cephalosporium, Escherichia, Flavobacterium, Kluvvera, Mycoplana, Protaminobacter, Pseudomonas and Xanthomonas, in particular *Acetobaxter pasteurianum, Bacillus megaterium, Escherichia coli* and *Xanthomonas citrii*.

Preferably an immobilized enzyme is used, since the enzyme can be easily isolated and re-used then. Immobilized enzymes are known as such and are commercially available. Example of suitable enzymes are the *Escherichia coli* enzyme from Boehringer Mannheim GmbH, which is commercially available under the name 'Enzygel®', the immobilized Penicillin-G acylase from Recordati, the immobilized Penicillin-G acylase from Pharma Biotechnology Hannover, and an *Escherichia coli* penicilline acylase isolated as described in WO-A-92/12782 and immobilised as described in EP-A-222462.

The enzymatic acylation reaction is mostly carried out at a temperature lower than 35° C., preferably between 0 and 28° C. The pH at which the enzymatic acylation reaction is carried out is mostly between 5.5 and 10, preferably between 6 and 9.

In practice the enzymatic acylation reaction and the working up of the reaction mixture are mostly carried out in water. Optionally, the reaction mixture may also contain an organic solvent or a mixture of organic solvents, preferably less than 30 vol. %. Examples of organic solvents that can be used are alcohols with 1–7 carbon atoms, for instance a monoalcohol, in particular methanol or ethanol; a diol, in particular ethylene glycol or a triol, in particular glycerol.

In the framework of the present invention the various components may be present in the reaction mixture in the free form or as salts. The pH values mentioned are in all cases the pH values measured at room temperature.

The invention will be further elucidated by means of the following examples, without however being restricted thereto.

Abbreviations
AMPI=ampicillin
AMPI.3H$_2$O=ampicillin trihydrate
6-APA=6-aminopenicillic acid
PGA=D-phenylglycine amide
PG=D-phenylglycine

EXAMPLE I

Enzymatic coupling of 200 mM of PGA and 200 mM of 6-APA at 5° C., followed by working up.

A mixture of 43.9 g of 6-APA and 30.6 g of PGA was suspended in 877 ml of water and cooled to 5° C. The resulting suspension was added to 100 g of 'wet' immobilized Pen-G acylase from Recordati (Milan). This enzyme is commercially available in a mixture of water and glycerol ('wet enzyme'); before use it was washed three times with 100 ml of water.

After 2 hours the pH had risen to 8.16. By means of concentrated aqueous NH$_3$ the pH was brought to 8.6 and after 5 minutes the reaction mixture was filtered through a G-3 glass filter; the residue was washed with 100 ml of water (5° C.). This residue was a mixture of enzyme and PG formed during the reaction.

The combined filtrate was acidified to pH 6.8 at 5° C. in 10 minutes by means of concentrated H$_2$SO$_4$. After 30 minutes, filtering, washing with 3×30 ml of water and drying were performed, which yielded 30.6 g of AMPI.3H$_2$O with a chemical purity (on a water-free basis) of >98%.

The mother liquor of the AMPI crystallization was again acidified to pH=4.6 with concentrated H$_2$SO$_4$ at 5° C. After stirring for 1 hour, filtering and washing with 2×20 ml of water were performed, which yielded 13.0 g of solid substance, calculated on a water-free basis. This solid substance contained a mixture of APA and AMPI in a molar ratio of 94:6.

EXAMPLE II

Enzymatic coupling of 200 mM of PGA and 200 mM of 6-APA at 5° C., followed by working up.

A mixture of 43.9 g of 6-APA and 30.6 g of PGA was suspended in 877 ml of water and cooled to 5° C. The resulting suspension was added to 100 g of 'wet' immobilized Pen-G acylase from Recordati (Milan). This enzyme is commercially available in a mixture of water and glycerol ('wet enzyme'); before use it was washed three times with 100 ml of water.

After 2 hours the pH had risen to 8.16. By means of concentrated aqueous NH$_3$ the pH was brought to 8.6 and after 5 minutes the reaction mixture was filtered through a G-3 glass filter; the residue was washed with 100 ml of water (5° C.). This residue was a mixture of enzyme and PG formed during the reaction.

The combined filtrate was worked up as follows: by means of a rotary film evaporator 510 ml of liquid was distilled off at 20° C. (in about 45–60 minutes), after which 510 ml of water was added. This procedure was repeated one time. The resulting suspension was filtered through a G-3 glass filter and washed with 2×30 ml of water (5° C.) and dried, which yielded 22.2 g of AMPI.3H$_2$O of a chemical purity (on a water-free basis) of >99%.

We claim:

1. A process for recovering ampicillin from a mixture containing ampicillin and 6-amino penicillic acid (6-APA) comprising:
   providing the mixture containing ampicillin and 6-APA, said mixture having an initial pH greater than 7 and being homogeneous at a pH between 7 and 8.5 apart from any solid ampicillin present; and
   lowering the initial pH of the mixture to a pH value above 5.5 and recovering ampicillin.

2. A process according to claim 1, wherein said lowering the pH is conducted without addition of organic solvents.

3. A process according to claim 1, wherein the initial pH is greater than 7.8 and the pH is lowered to a value between 5.5 and 7.8.

4. A process according to claim 1, wherein the mixture contains 2–60 mol % of 6-APA, calculated relative to the total amount of 6-APA and ampicillin.

5. A process according to claim 1, wherein the mixture contains 5–50 mol % of 6-APA, calculated relative to the total amount of 6-APA and ampicillin.

6. A process according to claim 1, wherein the process further comprises further lowering the pH of a first liquid phase remaining after recovering said ampicillin; and recovering a second solid substance.

7. A process according to claim 6, wherein the pH is further lowered to a pH between 1.5 and 6.

8. A process according to claim 6, wherein the process further comprises working up a second liquid phase which remains after said second solid substance is recovered; and recovering a third solid substance.

9. A process according to claim 1, wherein lowering the pH comprises adding a mineral acid to said mixture.

10. A process for recovering ampicillin from a mixture containing ampicillin and 6-amino penicillin acid (6-APA) comprising:
   obtaining a mixture containing ampicillin and 6-amino penicillin that is prepared from the reaction mixture of an enzymatic acylation reaction in which 6-APA is acylated using D-phenylglycineamide (PGA) or esters of D-phenylglycine, said mixture having an initial pH greater than 7; and
   reducing the pH of said mixture and crystallizing out ampicillin.

11. A process according to claim 10, wherein the enzymatic reaction is conducted using an immobilized enzyme.

12. A process according to claim 11, wherein in the enzymatic acylation reaction the pH is maintained by controlled addition of ammonia; and wherein said reducing the pH is accomplished by removing ammonia.

* * * * *